United States Patent [19]

Aid et al.

[11] Patent Number: 4,821,761
[45] Date of Patent: Apr. 18, 1989

[54] CLOSED LOOP PUMP CONTROL SYSTEM

[75] Inventors: James D. Aid, St. Petersburg; Shahid Q. Din, Clearwater; Andrew D. Hopping, Largo, all of Fla.

[73] Assignee: Baxter Travenol Laboratories, Inc., Deerfield, Ill.

[21] Appl. No.: 50,915

[22] Filed: May 15, 1987

[51] Int. Cl.[4] ............................................. G05D 11/13
[52] U.S. Cl. ................................ 137/101.21; 73/239; 137/99; 417/6
[58] Field of Search ....................... 137/101.21, 101.19, 137/99, 567; 73/239, 269, 861.77; 417/45, 413, 63, 6

[56] References Cited

U.S. PATENT DOCUMENTS

| | | |
|---|---|---|
| 2,772,664 | 12/1956 | Jones et al. .......................... 73/239 |
| 2,914,219 | 11/1959 | Chiantelassa .................. 137/567 X |
| 3,610,782 | 10/1971 | McGuire .......................... 417/45 X |
| 3,966,358 | 6/1976 | Heimes et al. ................... 417/45 X |
| 4,076,458 | 2/1978 | Jones ................................ 417/63 X |
| 4,119,113 | 10/1978 | Meginniss ............................. 137/99 |
| 4,176,672 | 12/1979 | Borberg .................... 137/101.21 X |
| 4,306,457 | 12/1981 | Fukui et al. ...................... 73/861.77 |
| 4,581,946 | 4/1986 | Kanayama ........................ 73/861.77 |

Primary Examiner—Stephen Hepperle
Attorney, Agent, or Firm—Paul C. Flattery; Charles R. Mattenson; Macdonald J. Wiggins

[57] ABSTRACT

A system for controlling the output flow rate of a second pump to proportionately track the output flow rate of a first pump in which the first pump produces an electrical signal at each successive stroke thereof. An electrical circuit produces an electrical control signal from the first pump stroke signal for controlling the flow rate of the second pump.

14 Claims, 2 Drawing Sheets

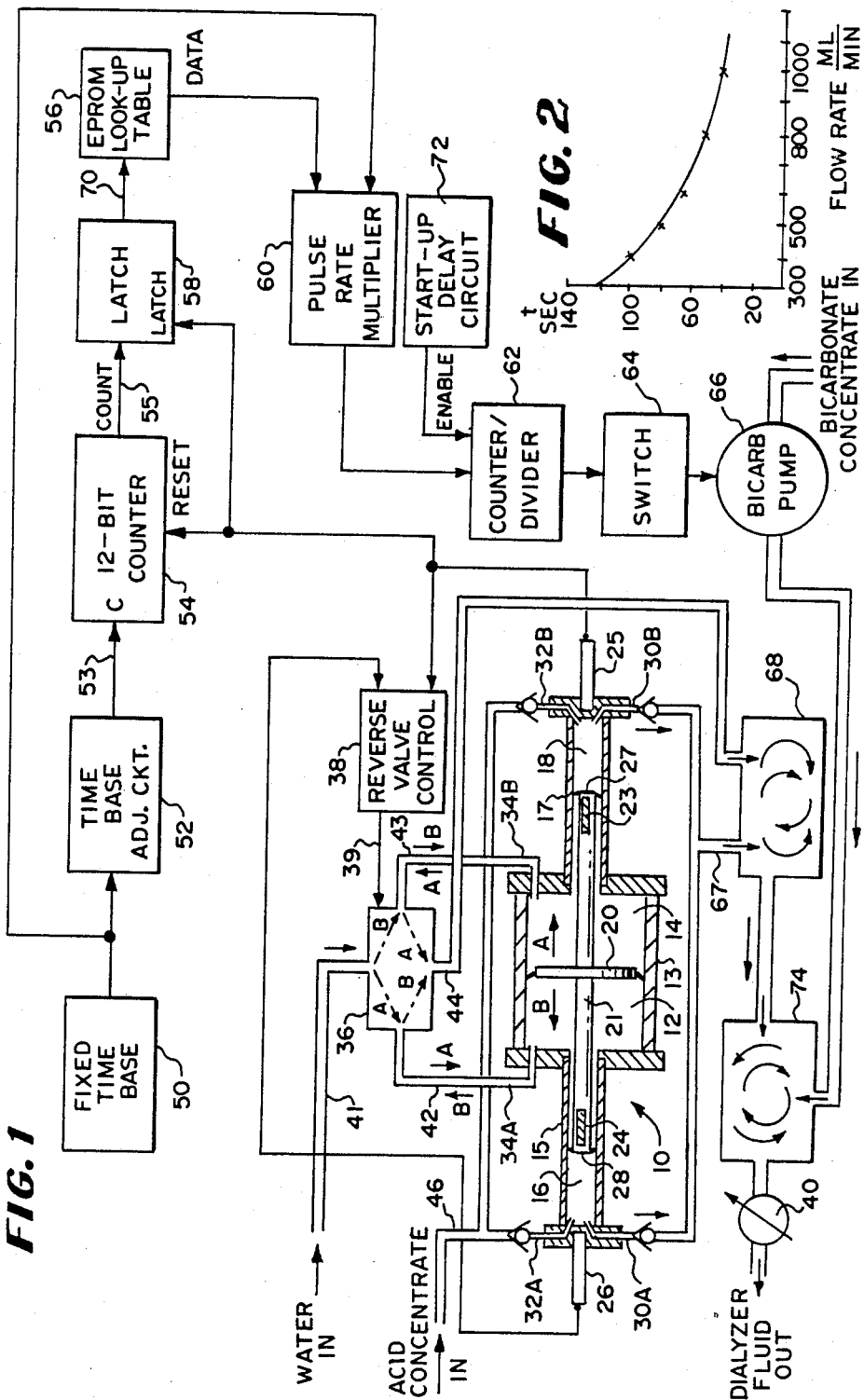

CLOSED LOOP PUMP CONTROL SYSTEM

BACKGROUND OF THE INVENTION

1. Field of the Invention

The present invention relates to a system having a pair of fluid pumps for accurately mixing solutions, and more particularly to a system in which one pump is controlled by the fluid flow of the other pump in a closed loop to ensure accuracy of mixing of the fluids.

2. Description of the Prior Art

Hemodialysis equipment is utilized to remove excess fluids from a patient's blood. Such equipment utilizes a dialyzer having a path through which the blood from the patient flows in and out to be returned to the patient. The blood flow chamber includes a semipermeable membrane through which water and low molecular weight solutes can pass but not blood cells. On the opposite side of the membrane, a dialysate chamber is provided through which a dialysate solution flows. The fluids passing through the membrane are picked up by the dialysate which flows out of the dialyzer. The removed fluids are known as filtrates.

A commonly used dialysate is prepared by diluting an acid concentrate with water and mixing the resulting solution with a measured amount of a bicarbonate solution to achieve a required conductivity level. Conductivity is an accepted method of determining that hemodialysis solutions are proportioned correctly. Preferably, such mixing process is performed continuously during treatment of a patient. In one hemodialysis apparatus, the acid concentrate is fed to a proportioning pump which also receives water as determined by a downstream flow control valve. The water-acid mixture is then mixed with a carefully metered amount of bicarbonate solution. The amount is preset based on the setting of the flow control valve and thus represents an open loop approach in which the accuracy is dependent upon a constant flow rate of the water-acid mixture from the proportioning pump.

A preferred proportioning pump is described in U.S. Pat. No. 4,119,113 to Meginniss, III which utilizes a double acting piston assembly to accurately mix precise quantities of water and acid concentrate. The pump is actuated by the water pressure, and the volume of concentrate and water produced on each stroke is constant. It is possible that the flow control valve used to control flow to the pump may drift or vary slightly with time. Since the ratio of acid to bicarbonate is determined by the flow rate from the proportioning pump, such variations will result in changes in the conductivity level of the dialysate.

Thus, a system for accurately controlling the mixing of the bicarbonate solution with the water-acid solution proportional to the flow rate of the water-acid solution in this type of hemodialysis apparatus is needed.

SUMMARY OF THE INVENTION

In a mixing system in which a concentrate is initially mixed with water and thereafter the mixture is mixed with a second concentrate, and in which the water-concentrate mixing portion of the system utilizes a proportioning pump operated by the pressure of the incoming water, the proportioning pump will produce a fixed volume of solution on each stroke thereof. Thus, the flow rate from the pump will vary with variations in the water pressure across the pump. When the water concentrate mixture is thereafter mixed with a second concentrate whose rate of flow is controlled by an electrical pump, which may be of the diaphragm type, the invention provides accurate control of the diaphragm pump so that the flow rate of the second concentrate bears a fixed ratio to the flow rate of the first porportioning pump.

The basic principal of the invention involves determining the time of a stroke of the first proportioning pump which will define the rate of flow of the water-concentrate mixture. The time period thus defined is utilized in an electronic control loop to control the flow rate of the diaphragm pump. Therefore, any variation in flow through the proportioning pump will produce a corresponding change in the flow rate from the diaphragm pump, maintaining the desired ratio of fluids.

The proportioning pump in this type of equipment utilizes a limit switch which is operated at each complete stroke. A signal is taken from such limit switch and used to reset a counter which may have sufficient counts to provide a desired accuracy of the system as will be more fully explained below. The counter will restart after the reset, and the count corresponding to one complete cycle of the proportioning pump will be latched and output into an erasable programmable read-only memory (hereinafter EPROM) programmed with a lookup table which will convert the time indicated by the count to a rate of flow measurement. As will be understood, the rate of flow is inversely proportional to the time of one cycle of the proportioning pump and is therefore a non-linear relationship. The lookup table therefore linearizes the time signal to produce the desired flow rate signal. The counter data is latched from the proportioning pump limit switch signal, then looked up in EPROM.

Although various types of pumps for the second concentrate may be used, where a diaphragm type pump is used which may be operated by a train of pulses, the output volume from the diaphragm pump may be controlled by varying the pulse rate of the electrical input to the diaphragm pump. Therefore, the flow rate data in the EPROM is utilized to control the pulse rate to the diaphragm pump. As will now be recognized, this control is effected on each stroke of the proportioning pump.

BRIEF DESCRIPTION OF THE DRAWINGS

FIG. 1 is a block diagram of the system of the invention; and

FIG. 2 is a typical plot of the function stored in the EPROM lookup table of FIG. 1.

DETAILED DESCRIPTION OF THE PREFERRED EMBODIMENT

The system of the invention provides a closed loop control system for use with a proportioning pump which pumps a fixed volume of fluid for each stroke to control a second pump producing a fixed volume with each stroke such that mixing of fluids from each pump can be made maintaining exactly the same ratio of fluids in the resulting mixture. It will be understood that the system of the invention will be applicable to any application requiring two fixed volume pumps in which accurate mixing of the outputs from each is required. However, the invention will be explained with reference to the dialysate system of a hemodialysis apparatus.

Referring to FIG. 1, a block diagram of the invention is presented with a double acting proportioning pump 10 shown in cross-sectional view and a second pump 66, which may be of the diaphragm type. Pump 10 is the type of pump disclosed in U.S. Pat. No. 4,119,113. In the system of FIG. 1, water under pressure is introduced to pump 10 via bistable solenoid valve 36. Solenoid valve 36 is controlled by valve control 38. Assuming that valve 36 is in a position such that flow of water from line 41 is in the direction of the dashed arrow A to line 42, water will enter chamber 12 of cylinder 13 via inlet 34A. The pressure of the water forces piston disc 20 in the direction shown by arrow A in cylinder chamber 14.

When valve control 38 controls solenoid valve 36 to direct water from line 41 in the direction of dashed arrow B, the water will flow through line 43 and inlet 34B into cylinder chamber 14 forcing the piston 20 in the direction as shown by arrow B in chamber 12. Valve 36 also connects water outlet line 44 as indicated by the dashed arrows such that when piston 20 is moving in direction A, water is forced out of chamber 14 via line 43 to output line 44; when piston 20 is moving in the direction B, water is forced from chamber 12 via valve 36 to output line 34. Thus, a double action operation occurs as piston 20 reciprocates. Reverse valve control 38 is controlled by magnetic switches 25 and 26. For example, when piston 20 is moving in direction A and reaches the end of its travel, a magnet 23 in piston rod 21 will actuate magnetic switch 25 causing reverse valve control 38 to reverse the position of solenoid valve 36 by a signal on line 39. Similarly, when piston 20 reaches the end of its travel in direction B, magnet 24 operates magnetic switch 26 which controls reverse valve control 38 to switch solenoid valve 36 to its other stable position. As will be noted, each stroke of pump 10 will displace exactly the same volume of fluid, in this case water, and the flow rate of the water in line 44 will depend upon the speed of operation of pump 10.

It will also be noted that the flow rate is therefore inversely proportional to the time of a stroke. Thus, the relationship between the flow rate and the time period of a stroke is shown in FIG. 2 for a typical pump 10 such as may be used in a dialysis equipment. For example, flow rates in the range of 300-1,000 milliliters per minute are commonly used. In addition to the pumping action of cylinder 13 and piston 10, a second set of double acting cylinders 17 and 15 is provided. Pistons 27 and 28 on either end of piston rod 21 act to provide a pumping action in chambers 16 and 18. Each of these chambers have a pair of input/output ports. Cylinder 15 has an input port 32A which is connected to an acid concentrate line 46 via a check valve. The other port is 30A and is connected by a check valve via line 67 to a mixing chamber 68. Similarly, cylinder 17 has input port 32 from line 46 via input check valve and an output port 30B connected to line 67 by an output check valve.

As may now be seen, an acid concentrate on line 46 will be drawn into chamber 16 when piston 20 is being moved in direction A by the incoming water pressure and the concentrate drawn into chamber 18 by a previous stroke will be forced outward via output 30B and line 67 to mixing chamber 68. Similarly, when piston 20 is moving in the direction shown by arrow B, the concentrate is drawn into chamber 18 and forced out of chamber 16 into mixing chamber 68. Thus, water flowing from line 44 into chamber 68 will mix with the acid concentrate flowing into chamber 68 on each stroke of pump 10. Since the volumes in chambers 12, 14, 16 and 18 are fixed, a fixed ratio of acid concentrate and water will be mixed in mixing chamber 68. This operation is known in the prior art as disclosed in U.S. Pat. No. 4,119,113.

To provide a dialyzer fluid, or dialysate, for a hemodialysis machine, it is required that the control of the conductivity of the dialysate be maintained very closely. To produce the dialysate, a bicarbonate concentration is mixed with the water and acid mixture from chamber 68. In the prior art, it has been necessary to carefully calibrate the pumping rate of bicarbonate pump 66 for the flow rate of the mixture from pump 10. Although this can be done when treatment with a dialysis machine has begun, the accuracy thereafter is dependent on the accuracy of flow controller valve 40. As will be recognized, any change in the flow of water on line 41 will result in a change in the time of a stroke of pump 10 and therefore the flow rate into chamber 68 will vary. As will be described, the system of the invention controls the flow rate from bicarbonate pump 66 in direct proportion to the time of a stroke of pump 10. Therefore, any variation in the input water pressure or flow rate will not change the calibrated ratio between the amount of bicarbonate concentrate from pump 66 and the acid/water mixture from chamber 68.

A digital control system is utilized having a fixed time base generator 50 which has its output connected to a rate multiplier 60. Time base 50 produces a sequence of pulses at a fixed rate. Pulse rate multiplier 60 changes the number of pulses per second to be directly proportional to the time of a stroke of pump 10. Bicarbonate pump 66, which is a fixed volume type pump such as a diaphragm type, will therefore produce a variable output flow rate depending upon the number of pulses per second which it receives. Thus, the output from pulse rate multiplier 60 is utilized via counter divider circuit 62 to control switch 64, which is preferably a solid state type switch. Switch 64 drives pulse pump 66 at the required output flow rate. To control pulse rate multiplier 60, a 12-bit counter 54 is utilized. As will be recognized, a full count of counter 54 will produced 4096 counts. However, counter 54 will be reset before it reaches its full count by the same signal which operates reverse valve control 38 from magnetic switch 25. Thus, counter 54 is reset once on each double stroke of pump 10. Time base adjust circuit 52 is provided to compensate for variations in pumps 10 and other elements of the water/acid concentrate system. Variable time base 52 is adjusted such that in the stroke time of pump 10, counter 54 will not reach its full count but will reset at some intermediate point. Thus, as the pump 10 stroke time varies due to variations in the input water flow, counter 54 will be producing a varying output count on lead 55.

When piston 20 reaches the end of its travel in the direction of arrow A, magnetic switch 25 actuates, latching count value in latch 58 and resetting counter 54. As piston 20 moves in the direction of arrow B, reverses and moves back in the direction of arrow A, counter 54 will be running from the time base signal on lead 53 and will reach a certain count when switch 25 is next closed. This count, when latched, appears on lead 70 and is directly proportional to the time of the previous stroke. An EPROM 56 is programmed with a lookup table which reproduces the stroke time to flow rate relationship as shown in FIG. 2. For a given latched count on lead 70, EPROM 56 outputs a digital number representative of the flow rate of pump 10. The output data from EPROM 56 is input to pulse rate multiplier 60 which will vary the pulse rate from fixed time base 50 in an amount directly proportional to the flow rate. Bicarbonate pump 66 is thereby controlled to produce an output flow rate which will vary directly with the variation in flow rate from pump 10 and will therefore track pump 10.

Start-up delay circuit 72 is utilized to disable counter divider 62 by one full stroke of pump 10 so that, on initial startup, chambers 12 and 14 can both fill with water and the acid chambers 16 and 18 with acid concentrate before control begins.

The acid water mixture in mixing chamber 68 flows into dialysate mixing chamber 74 along with the bicarbonate concentrate from bicarbonate pump 66 and is mixed in chamber 74. The dialyzer fluid output connects to the dialyzer via flow control valve 40 in the hemodialysis machine and will have the proper conductivity for operation thereof.

It will also be recognized that, in the prior art dialysate mixing systems, the user is limited to a set flow rate of, for example, 500 milliliters per minute without manual recalibration of the bicarbonate pump. The system of the invention permits any dialysate flow rate between, for example, 300-1,000 milliliters per minute without recalibration of the bicarbonate pump being required. Additionally, the system of the invention will adjust the bicarbonate input as described to compensate for drifts in the dialysate flow controller.

Although the pump control system of the invention has been disclosed with reference to dialysate pumps in a hemodialysis apparatus, such application is for exemplary purposes only. The invention is applicable to any dual pump mixing systems in which one pump is required to accurately track the flow rate of another pump. Variations in the system may be made without departing from the spirit or scope of the invention.

We claim:

1. In a fluid mixing system having a first proportioning pump that pumps a fixed volume of a first fluid on each stroke thereof and a second electrically operated pump having a flow rate of a second fluid that is directly proportional to the comprising:
   an electrical limit switch operatively connected to said first pump and actuated at each stroke thereof;
   a mixing chamber connected to said first pump for receiving said first fluid, and connected to said second pump for receiving said second fluid to thereby effect mixing of said first and second fluids;
   electrical timing means connected to said limit switch for producing first electrical data directly proportional to the time between successive actuations of said limit switch; and
   nonlinear conversion means connected to said timing means for converting said first electrical time data therefrom to second electrical data directly proportional to the rate of flow of said first fluid during each successive stroke of said first pump;
   electrical control means connected to control the rate of flow of said second fluid from said second pump, said control means connected to said conversion means for receiving said second electrical flow rate data;
   whereby a fixed ratio of said first fluid to said second fluid is maintained in said mixing chamber.

2. The system as recited in claim 1 in which said timing means includes:
   a digital counter having a reset operatively connected to receive a reset signal from said limit switch; and
   a time base connected to a counting input of said counter for generating a fixed rate pulse train for actuating said counter.

3. The system as recited in claim 2 in which said electrical control means includes an electrical latch circuit connected to said counter for storing said flow rate data during a stroke of said first pump, said latch circuit controlled by said reset signal.

4. The system as recited in claim 3 in which:
   said conversion means includes a digital lookup table for receiving a count from said electrical latch circuit when said counter is reset, and for producing said second electrical flow rate data from said count; and
   means for varying said electrical input to said second pump responsive to said flow rate data signal.

5. The system as recited in claim 4 in which:
   said electrical input to said second pump is a train of pulses; and
   said means for varying said electrical input is a pulse rate multiplier.

6. A system for controlling the output flow rate of a second pump according to a predetermined nonlinear profile to track the output flow rate of a first pump comprising:
   a positive displacement piston pump having an output flow rate inversely proportional to the period of time of one stroke of said pump;
   an electrically operated diaphragm pump having an output flow rate directly proportional to the electrical energy applied thereto;
   means connected to said piston pump for producing a first electrical signal directly proportional to the period of time of each successive stroke of said piston pump; and
   means receiving said first electrical signal for producing therefrom, in accordance with a predetermined nonlinear profile, a second electrical signal directly proportional to said output flow rate of said piston pump, said second electrical signal connected to said diaphragm pump to thereby cause said output flow rate thereof to proportionally track said output flow rate of said piston pump.

7. In a fluid mixing system having a first proportioning pump, said first pump having a piston which pumps a fixed volume of a first fluid on each stroke thereof, said first pump operated by water pressure subject to variations in pressure, the flow rate of said first fluid being a function of said water pressure, a second electrically driven pump having a flow rate of a second fluid, said second pump having a flow rate being a function of the rate of an electrical pulse train input thereto, and a mixing chamber for receiving said first fluid and said second fluid, the improvement comprising:
   a limit switch actuated at the end of a stroke of said piston for producing an electrical pulse for each stroke;
   counting means connected to said limit switch for producing a count proportional to the time of a cycle of said first pump; and
   means connected to said counting means for converting said count to a measurement of rate of flow of said first fluid, said measurement being a train of electrical pulses having a pulse repetition rate inversely, proportional to said time of a cycle of said first pump, said converting means connected to drive said second pump to produce a flow rate of said second fluid directly proportional to the flow rate of said first fluid.

8. A fluid mixing system for mixing a first solution of a first fluid and water, thereby producing a first solution, and thereafter mixing the first solution with a second fluid comprising:

a first double piston pump having a first piston thereof driven by input water under pressure and outputting a fixed volume of water on each stroke thereof and having a second piston outputting a fixed volume of said first fluid on each stroke thereof;

limit switch means for producing an electrical pulse for each stroke, the time between successive pulses being inversely proportional to the rate of flow of said water and said first fluid from said first pump;

a first mixing chamber connected to receive said outputted water and said outputted first fluid from said first pump, said chamber having an output for said first solution; and a second fixed volume electrical pulse driven pump producing an output flow rate of a second fluid directly proportional to the rate of electrical driving pulses;

a second mixing chamber having a first input connected to said output of said first mixing chamber to receive said first solution, and a second input connected to receive said second fluid from said second pump; and conversion means connected to receive a fluid sequence of said successive pulses for producing therefrom a second sequence of pulses for driving said pulse driven pump having a pulse rate directly proportional to the rate of flow of water from said first pump whereby a preselected ratio of mixing of said second fluid and said first solution is maintained with changes in pressure of said water.

9. The system as recited in claim 8 in which said limit switch means includes:

a normally open switch adapted to be closed by said piston in said first pump at the end of its stroke; and a source of electrical current connected to said switch.

10. A fluid mixing system for accurately mixing a first fluid with water supplied under pressure to form a first solution, and for accurately mixing a second fluid with said first solution to form a second solution comprising:

(a) a proportioning pump having
  (i) a double action piston assembly having a first double piston operated by said water under pressure is a first pair of chambers;
  (ii) a second double piston operatively connected to said first double piston and moving in a second pair of pump chambers for pumping said first fluid, and
  (iii) a limit switch operable by said piston assembly at each stroke thereof to produce an electrical pulse;

(b) a first mixing chamber for receiving a fixed amount of water from one of said first pump chamber and a fixed amount of said first fluid from one of said second pump chambers during each stroke of said proportioning pump, said water and said first fluid mixing to form said first solution;

(c) an electrically operated diaphragm pump having an output flow rate directly proportional to the electrical energy applied thereto, said diaphragm pump for pumping said second fluid;

(d) means for receiving a sequence of electrical pulses from said limit switch and for nonlinearly converting said sequence to an electrical control signal directly proportional to the rate of flow of said water from said chambers during each successive stroke of said proportioning pump;

(e) electrical control means connected to said diaphragm pump and receiving said electrical control signal from said converting means whereby said diaphragm pump output flow rate of said second fluid is in a fixed ratio to the flow rate of said first solution; and (f) a second mixing chamber connected to receive said first solution from said first mixing chamber and said second fluid from said diaphragm pump, said second fluid and said first solution mixing to form said second solution.

11. The system as recited in claim 10 in which said receiving and converting means includes:

a digital counter having a reset operatively connected to receive a reset signal from said limit switch; and a time base connected to a counting input of said counter for generating a fixed rate pulse train for actuating said counter.

12. The system as recited in claim 11 in which said receiving and converting means includes:

an electrical latch circuit connected to said counter for storing said flow rate data during a stroke of said first pump, said latch circuit controlled by said reset signal.

13. The system as recited in claim 12 in which said receiving and converting means includes:

a digital lookup table for receiving a count from said electrical latch circuit when said counter is reset, and for producing said second electrical control signal from said count; and means for varying said electrical input to said second pump responsive to said control signal.

14. The system as recited in claim 13 in which:

said electrical control signal to said second pump is a train of pulses; and said means for varying said electrical input is a pulse rate multiplier.

* * * * *